United States Patent
Izumori et al.

(10) Patent No.: US 8,227,232 B2
(45) Date of Patent: Jul. 24, 2012

(54) THERMOSTABLE L-RIBOSE ISOMERASE AND METHOD FOR PRODUCING SAME AND USE OF SAME

(75) Inventors: Ken Izumori, Kita-gun (JP); Kenji Morimoto, Kita-gun (JP); Goro Takata, Kita-gun (JP); Masaaki Tokuda, Kita-gun (JP); Yoshio Tsujisaka, Kita-gun (JP); Kei Takeshita, Marugame (JP); Keiji Tsusaki, Okayama (JP); Kazuhiro Okuma, Itami (JP)

(73) Assignees: National University Corporation Kagawa Univeristy, Takamatsu-shi (JP); Rare Sugar Production Technical Research Laboratories, LLC., Kita-gun (JP); Matsutani Chemical Industry Co., Ltd., Itami-shi (JP)

( * ) Notice: Subject to any disclaimer, the term of this patent is extended or adjusted under 35 U.S.C. 154(b) by 421 days.

(21) Appl. No.: 12/515,596

(22) PCT Filed: Mar. 26, 2007

(86) PCT No.: PCT/JP2007/056167
§ 371 (c)(1),
(2), (4) Date: Sep. 16, 2009

(87) PCT Pub. No.: WO2008/062569
PCT Pub. Date: May 29, 2008

(65) Prior Publication Data
US 2009/0325231 A1    Dec. 31, 2009

(30) Foreign Application Priority Data
Nov. 20, 2006 (JP) ................. 2006-313673

(51) Int. Cl.
*C12N 9/90* (2006.01)
*C12N 1/00* (2006.01)
*C12P 19/24* (2006.01)
*C07H 1/00* (2006.01)
*C07H 1/06* (2006.01)

(52) U.S. Cl. ......... 435/233; 435/243; 435/94; 536/1.11; 536/124; 536/125; 536/127

(58) Field of Classification Search .................. 435/233, 435/243, 94; 536/1.11, 124, 125, 127
See application file for complete search history.

(56) References Cited

FOREIGN PATENT DOCUMENTS
KR    10-2005-0064991 A    6/2005

OTHER PUBLICATIONS

Drancourt et al., Phylogenetic analyses of *Klebsiella* species delineate *Klebsiella* and *Raoultella* gen. nov., . . . Int. J. System. Evol. Microbiol., 2001, vol. 51: 925-932.*
Mizanur et al., Cloning and characterization of a novel gene encoding L-ribose isomerase from *Acinetobacter* sp. strain DL-28 in *Escherichia coli.*, Biochim. Biophys. Acta., 2001, vol. 1521: 141-145.*
Shimonishi et al., A new enzyme, L-ribose isomerase from *Acinetobacter* sp., strain DL-28. J. Ferment Eng., 1996, vol. 81 (6): 493-497.*
Broun et al., Catalytic plasticity of fatty acid modification enzymes underlying chemical diversity of plant lipids. Science, 1998, vol. 282: 1315-1317.*
Kisselev L., Polypeptide release factors in prokaryotes and eukaryotes: same function, different structure. Structure, 2002, vol. 10: 8-9.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Shimonishi et al. "A New Ezyme, L-Ribose Isomerase from *Acinetobacter* sp. Strain DL-28", Journal of Fermentation and Bioengineering, pp. 493-497, 1996, vol. 81, No. 6.

* cited by examiner

*Primary Examiner* — Ganapathirama Raghu (57) ABSTRACT

Object: To provide a thermostable L-ribose isomerase.
Means for Resolution: The thermostable L-ribose isomerase with MW. 32,000 (by SDS-PAGE), optimal temperature of 45° C., optimal pH of pH 9.0 (glycine-NaOH buffer), and stable physicochemical properties such as temperature stability up to 45° C. during thermal treatment at pH 9.0 for 10 minutes, and with an action to isomerize L-ribose to generate L-ribulose or of inversely to isomerize L-ribulose to generate L-ribose. A conversion method between an aldose and a ketose comprising allowing the thermostable L-ribose isomerase as an enzyme derived from (1) *Raoultella ornithinolytica* strain MB426 (NITE BP-277) to interact with an aldose selected from L-ribose, D-lyxose, D-tallose, D-mannose, L-allose and L-gulose to isomerize the aldose to generate a ketose selected from the individually corresponding L-ribulose, D-xylulose, D-tagatose, D-fructose, L-psicose and L-sorbose or to interact with a ketose selected from L-ribulose, D-xylulose, D-tagatose, D-fructose, L-psicose and L-sorbose to isomerize the ketose to generate an aldose selected from the individually corresponding L-ribose, D-lyxose, D-tallose, D-mannose, L-allose and L-gulose.

14 Claims, 4 Drawing Sheets

THERMOSTABLE L-RIBOSE ISOMERASE AND METHOD FOR PRODUCING SAME AND USE OF SAME

TECHNICAL FIELD

The present invention relates to a thermostable L-ribose isomerase, a method for producing the same and the use of the same. More specifically, the invention relates to a thermostable L-ribose isomerase which isomerizes L-ribose to L-ribulose or to isomerize L-ribulose to L-ribose, a method for producing the thermostable L-ribose isomerase, a microorganism generating the L-ribose isomerase, and a method for producing ketose and aldose using the enzyme.

BACKGROUND ART

Following the development of biochemical industries, recently, attention has been increasingly raised toward the biological activities of rare sugars in the field of sugar chemistry (non-patent reference 1), so that demands toward various types of rare sugars conventionally never needed are now occurring. Therefore, the establishment of a method for stably producing these sugars has been desired. The method for producing these sugars may be done by approaches of organic chemistry. Generally, however, the conditions for the production by the approaches are very tough at very low yields of intended sugars, inappropriately as an industrial production method. As a biochemical approach, alternatively, sugar conversion methods with enzymes are listed. As described in the patent reference 1 for industrial production of L-ribose, the present inventors made a success in developing a milestone therefor. The inventors made further investigations regarding the production and utilization of L-ribose isomerase. Based on the partial amino acid sequence of L-ribose isomerase as disclosed in the patent reference 1, the inventors made diverse examinations about the chromosomal DNAs of microorganisms capable of generating the enzyme. Consequently, the inventors found that DNA encoding a series of amino acid sequences including the partial amino acid sequence was successfully cloned from a microorganism of the genus *Acinetobacter* (patent reference 2). Using the cloned DNA, then, the inventors made attempts to prepare a recombinant polypeptide, so that the inventors confirmed that a polypeptide with the activity of L-ribose isomerase could efficiently be produced.

Patent reference 1: JP-A-10-155480
Patent reference 2: JP-A-2002-253254
Non-patent reference 1: Rare Sugar Congress in Kagawa: 2005. Proc $2^{nd}$ Symp Int Soc Rare Sugars, Takamatsu, Japan.

DISCLOSURE OF THE INVENTION

Problems that the Invention is to Solve

In terms of the upsurge of the recent demand toward L-ribose, a method for preparing an enzyme generating L-ribose should be established while the properties of such enzyme should be improved further. In industrially producing sugars, it is strongly desired to establish a method for producing sugars of types as many as possible, using enzymes of types of a number as small as possible. It is an object of the invention to screen for a microorganism with properties advantageous for the method for industrially producing rare sugars such as L-ribose and D-tallose and with an ability to generate an enzyme capable of producing sugars of diverse types.

Furthermore, it is an object of the invention to provide an enzyme derived from the microorganism, which has a property useful for isomerizing L-ribose to generate L-ribulose or isomerizing L-ribulose to generate L-ribose and an ability to use various types of ketose or aldose as the substrate, as well as a method for producing ketose and aldose using the enzyme.

Means for Solving the Problems

The gist of the invention resides in a thermostable L-ribose isomerase described below in (1) through (4).
(1) A thermostable L-ribose isomerase with the following physico-chemical properties and with an action to isomerize L-ribose to generate L-ribulose or to isomerize L-ribulose to generate L-ribose inversely:
 1) molecular weight: 32,000 (SDS-PAGE);
 2) optimal temperature: 45° C.;
 3) optimal pH: pH 9.0 (glycine-NaOH buffer);
 4) temperature stability: stable up to 45° C., during thermal treatment at pH 9.0 for 10 minutes.
(2) The thermostable L-ribose isomerase described in (1), where the L-ribose isomerase is an enzyme derived from a microorganism belonging to the genus *Raoultella*.
(3) The thermostable L-ribose isomerase described in (2), which is an enzyme derived from a microorganism belonging to *Raoultella ornithinolytica*.
(4) The thermostable L-ribose isomerase described in (2), which is an enzyme derived from the bacterial strain MB426 (NITE BP-277) of the genus *Raoultella*.

The gist of the invention resides in a method for producing L-ribose isomerase as described below in (5) to (8).
(5) A method for producing a thermostable L-ribose isomerase comprising culturing a microorganism with an ability to generate L-ribose isomerase, and collecting a thermostable L-ribose isomerase with the following physico-chemical properties and with an action to isomerize L-ribose to generate L-ribulose or to isomerize L-ribulose to generate L-ribose inversely, from the culture:
 1) molecular weight: 32,000 (SDS-PAGE);
 2) optimal temperature: 45° C.;
 3) optimal pH: pH 9.0 (glycine-NaOH buffer);
 4) temperature stability; stable up to 45° C., during thermal treatment at pH 9.0 for 10 minutes.
(6) The method for producing a thermostable L-ribose isomerase as described in (5), where the microorganism is a microorganism belonging to the genus *Raoultella*.
(7) The method for producing a thermostable L-ribose isomerase as described above in (6), where the microorganism is a microorganism belonging to *Raoultella ornithinolytica*.
(8) The method for producing a thermostable L-ribose isomerase as described above in (6), where the thermostable L-ribose isomerase is an enzyme derived from the bacterial strain MB426 (NITE BP-277) of the genus *Raoultella*, The gist of the invention is a microorganism belonging to the genus *Raoultella* as described below in (9) or (10).
(9) A microorganism belonging to the genus *Raoultella* and with the following physico-chemical properties and with an ability to generate a thermostable L-ribose isomerase with an action to isomerize L-ribose to generate L-ribulose or to isomerize L-ribulose to generate L-ribose inversely:
 1) molecular weight: 32,000 (SDS-PAGE);
 2) optimal temperature: 45° C.;
 3) optimal pH: pH 9.0 (glycine-NaOH buffer);
 4) temperature stability; stable up to 45° C., during thermal treatment at pH 9.0 for 10 minutes.

(10) The microorganism as described above in (9), where the microorganism of the genus *Raoultella* is *Raoultella ornithinolytica* MB426 (NITE BP-277) or a variant strain thereof.

The gist of the invention resides in a method for producing a ketose as described below in (11) or (12).

(11) A method for producing a ketose, comprising allowing the thermostable L-ribose isomerase described above in (1), (2), (3) or (4) to interact with an aldose selected from L-ribose, D-lyxose, D-tallose, D-mannose, L-allose, and L-gulose and collecting a ketose selected from the individually corresponding generated L-ribulose, D-xylulose, D-tagatose, D-fructose, L-psicose and L-sorbose.

(12) The method for producing a ketose as described above in (11), where the thermostable L-ribose isomerase is an enzyme obtained by toluene treatment of a microorganism with the activity of a thermostable L-ribose isomerase and/or is an immobilized enzyme.

The gist of the invention resides in a method for producing an aldose as described below in (13) or (14).

(13) A method for producing an aldose, comprising allowing the thermostable L-ribose isomerase described above in (1), (2), (3) or (4) to interact with a ketose selected from L-ribulose, D-xylulose, D-tagatose, D-fructose, L-psicose and L-sorbose and collecting an aldose selected from the individually corresponding generated L-ribose, D-lyxose, D-tallose, D-mannose, L-allose and L-gulose.

(14) The method for producing an aldose as described above in (13), where the thermostable L-ribose isomerase is an enzyme obtained by toluene treatment of a microorganism with the activity of a thermostable L-ribose isomerase and/or is an immobilized enzyme.

The gist of the invention resides in a conversion method between an aldose and a ketose, as described below in (15) or (16).

(15) A conversion method between an aldose and a ketose, comprising allowing a thermostable L-ribose isomerase described above in (1), (2), (3) or (4) to interact with an aldose selected from L-ribose, D-lyxose, D-tallose, D-mannose, L-allose, and L-gulose to isomerizes the aldose to corresponding a ketose selected from L-ribulose, D-xylulose, D-tagatose, D-fructose, L-psicose and L-sorbose or comprising allowing a thermostable L-ribose isomerase described above in (1), (2), (3) or (4) to interact with a ketose selected from L-ribulose, D-xylulose, D-tagatose, D-fructose, L-psicose and L-sorbose to isomerizes the ketose to corresponding an aldose selected from L-ribose, D-lyxose, D-tallose, D-mannose, L-allose and L-gulose.

(16) The conversion method between an aldose and a ketose as described above in (15), where the thermostable L-ribose isomerase is an enzyme obtained by toluene treatment of a microorganism with the activity of a thermostable L-ribose isomerase and/or is an immobilized enzyme.

The gist of the invention resides in a method for producing L-ribose as described below in (17) to (21).

(17) A method for producing L-ribose comprising a step of allowing the thermostable L-ribose isomerase described in (1), (2), (3) or (4) to interact with L-ribulose and a step of colleting the generated L-ribose.

(18) The method for producing L-ribose, as described in (17), where the L-ribulose is obtained by oxidizing ribitol with a microorganism belonging to the genus *Glucobacter* or the genus *Acetobacter*.

(19) The method for producing L-ribose as described above in (17) or (18), where the thermostable L-ribose isomerase is obtained by toluene treatment of a microorganism with the activity of a thermostable L-ribose isomerase and/or is an immobilized enzyme.

(20) The method for producing L-ribose as described in (17), (18), or (19), where the generated L-ribose is collected through a step including filtration, centrifugation, decoloring, desalting, concentration, drying, column chromatography, crystallization and/or sugar fractionation.

(21) The method for producing L-ribose as described above in (20), where an ion exchange resin is used for column chromatography.

Advantages of the Invention

Since L-ribose isomerase obtained conventionally has poorly thermostable and is inactivated during isomerization reactions, a method comprising treating the bacterial cell with toluene and immediately using the resulting bacterial cell is utilized. By the method, the bacterial cell cultured each time can be used only once, so such method is not suitable for producing L-ribose at a mass scale. Therefore, the enzyme at high stability is needed. It is desired to construct a bioreactor using such thermostable enzyme.

So as to screen for a microorganism with thermostable L-ribose isomerase, various soil types are added to a culture medium of inorganic salts and with L-ribose as a carbon source, for culturing at a relatively high temperature to isolate the microorganism, so that it has been expected to obtain L-ribose isomerase with higher thermostability than those of the existing enzymes. However, it was difficult so far to isolate a microorganism generating L-ribose isomerase. The main reason is as follows: L-ribose was so expensive that L-ribose at an amount sufficient enough for separating numerous types of microorganisms from numerous sources for such separation could not be prepared.

Using the L-ribose isomerase already separated as described in the patent reference 1, the present inventors could obtain a sufficient amount of L-ribose. Hence, the L-ribose for use in accordance with the invention could be prepared, which enabled the recovery of the intended microorganism.

As a method for isolating a strain generating L-ribose isomerase, a method for screening for such microorganism from various separation sources was an effective method, which comprised culturing with L-ribose as a carbon source to assay the generated L-ribulose in the liquid culture resulting from the culturing at a high sensitivity by the cysteine-carbazole method and subsequently using the assay results of the generated L-ribulose as a marker.

The thermostable L-ribose isomerase of the invention is advantageously used in converting a great number of sugars with no need of high purification, so such L-ribose isomerase can advantageously be used for industrial production of rare sugars. In accordance with the invention, a great number of rare sugars extremely hardly available conventionally can be provided efficiently in a ready manner. Accordingly, it is expected that the enzyme would give influences on diverse fields such as foods, cosmetics, pharmaceutical products and chemical industries. Thus, the enzyme has an extremely significant meaning industrially.

BEST MODE FOR CARRYING OUT THE INVENTION

So as to solve the problems, the inventors made screenings for a wide variety of microorganisms generating an enzyme interactive with sugars of various types as many as possible, particularly with attention focused on L-ribose isomerase. Consequently, the inventors found that the strain MB426 isolated in soils in a river bed in Miki-cho, Kida-gun, Kagawa, Japan was a novel microorganism of the genus *Raoultella* to generate a novel L-ribose isomerase interactive with various types of sugars at a mass scale, which had relatively high optimal temperature and thermostability, high stability at the optimal pH, extremely advantageously for industrial utilization of the enzyme. Additionally, the inventors found that a great number of rare sugar types could be produced readily via the interaction of a solution containing a substrate ketose or aldose with the microorganism. Thus, the invention has been achieved.

The strain MB426 isolated by the inventors is a novel microorganism belonging to the genus *Raoultella*.

The bacterial strain "*Raoultella ornithinolytica* MB426" as a novel microorganism in accordance with the invention is a bacterial strain of the *Raoultella ornithinolytica* and was deposited domestically in Japan at Incorporated Administrative Agency, National Institute of Technology and Evaluation, Patent Microorganism Depositary, 2-5-8 Kamatari Kazusa, Kisarazu-shi, Chiba, Japan, for which an accession certificate was issued as an accession No. (NITE AP-277) on Nov. 13, 2006. In filing an international application, currently, it was requested to transfer the original deposit (NITE AP-277) to the international depositary organization to which the original deposition was made. On Mar. 22, 2007, an accession certificate (NITE BP-277) was issued for the original deposit by the international depositary organization.

For isolation of the strain MB426, the microorganism was separated at 37° C. in a culture broth of inorganic salts containing 0.5 w/w % L-ribose as a single carbon source. The bacterial strain growing under the conditions and generating L-ribose isomerase was separated. In the agar culture medium for use in the isolation and storage of the microorganism, a culture medium of inorganic salts using L-ribose as a single carbon source was used.

The enzyme-generating ability of the separated bacterial strain, the conditions for the enzyme generation and the like were examined. Consequently, the inventor found that L-ribose isomerase could be produced in a stable manner at a mass scale, using the inexpensive carbon source. Specifically, the inventor found that the enzyme could be generated at a mass scale, even when a culture broth supplemented with a small amount (0.1% to 3%, preferably 0.1 to 0.5%) of D-lyxose added to 2% TSB (tryptic soy broth) or the TSB culture medium with no addition of D-lyxose was used.

The DNA of the 16S rRNA region extracted from the bacterial strain was sequenced, and compared with those of plural types of known 16S rRNAs obtained from other microorganisms. The data was 97-% identical to the sequence derived from *Raoultella ornithinolytica*. Based on the evidence and other physiological features described in Table 2, it was concluded that the bacterial strain corresponded to *Raoultella ornithinolytica*. The nucleotide sequence of a DNA fragment can be sequenced by known methods, for example the Sanger method (Molecular Cloning, Vol. 2, p. 13.3, 1989), and PCR-based methods. Generally, the reaction is performed with GenomeLab DTCS Quick Start Kit (sequencing kit containing fluorescence dideoxy terminator) manufactured by Beckman Coulter, to determine the sequence of the nucleotide sequence with an automatic sequence (CEQ 8000, etc.) of Beckman Coulter.

Table 1 shows the results of the identification test of the microbial strain MB426 of the genus Raoultella in accordance with the invention.

TABLE 1

*Raoultella ornithinolytica* strain MB426

Gram staining: negative
Motility: none
Growth temperature: 37° C. (possibly growing at 4 up to 40° C.; preferably at 37° C.)
Oxygen demand: aerobic
Morphology: long rod
Colonies at growth state: semi-transparent, pale yellow colonies formed.

Culture Medium (Culturing at for example pH 5 to 9, preferably pH 6 to 8.5. Culturing is done under aerobic conditions, including for example shaking culture or aerated agitation culture).

1. Tsb (Tryptic Soy Broth) Culture Medium 1 to 2%

TSB: Becton, Dickinson Co., Ltd.

2. Meat Extract Culture Medium

[meat extracts (Wako Pure Chemical Industry Co., Ltd.) 0.5%, polypeptone (Wako Pure Chemical Industry Co., Ltd.) 0.5%, sodium chloride (Wako Pure Chemical Industry Co., Ltd.) 0.5%, pH 7.0]

3. Yeast Extract Culture Medium

[yeast extracts (Wako Pure Chemical Industry Co., Ltd.) 0.5%, polypeptone (Wako Pure Chemical Industry Co., Ltd.) 0.5%, sodium chloride 0.5%, pH 7.0]

4. Composition of Culture Medium of Inorganic Salts 0.26% ammonium sulfate, 0.24% $KH_2PO_4$, 0.56% $K_2HPO_4$, 0.01% magnesium sulfate, 0.05% yeast extract In case of an agar culture medium, agar is added to a final concentration of 2% to the culture media described above.

<A. Cell morphology> (TSB agar culture medium at 37° C.) Generally, long rod with a diameter of 0.3 to 1.0 μm and a length of 0.6 to 6.0 μm. No motility. No spore. Gram negative.

<B. Culturing properties> (Meat juice agar plate culture at 37° C.) Morphology: circle. The size is 0.1 to 5 mm after 2-day culturing. Periphery: whole fringe. Protrusion: semi-lens state. Gloss: blunt. Surface: smooth. Color: opaque, pale yellow.

In accordance with the invention, not only the bacterial strain described above but also other bacterial strains of *Raoultella* and with an ability to generate L-ribose isomerase and variant strains thereof may also be used appropriately.

Any culture medium in which the microorganism can grow to generate L-ribose isomerase of the invention may be used as the culture medium for use in culturing the microorganism of the invention, which may satisfactorily be a synthetic medium or a natural medium. As the carbon source, for example, one type or two types or more selected from aldose, ketose and the like may appropriately be selected. As the nitrogen source, for example, inorganic nitrogen compounds such as ammonium salts and nitrate salts, and organic nitrogen-containing materials for example urea, corn steep liquor, casein, peptone, yeast extract and meat extract may be used. As the inorganic ingredients, additionally, calcium salts, magnesium salts, potassium salts, sodium salts and phosphate salts may appropriately be used. Any culture conditions under which the microorganism can grow to generate the enzyme of the invention are appropriate and are generally at a temperature and a pH selected from about 4 to 40° C., preferably about 20 to 37° C., and pH about 5 to 9, preferably about 6 to 8.5.

In such manner, the microorganism is cultured to recover the enzyme of the invention from the resulting culture. The activity of the enzyme is mainly observed in the bacterial cell, so the bacterial cell itself may also be used as an enzyme agent or the whole culture may also be used as an enzyme agent. The enzyme in the bacterial cell may be extracted from the bacterial cell by general methods, which may also be used as a crude enzyme. The crude enzyme may be used as it is, but the crude enzyme may further be purified by general methods. For example, an extract solution from disruption of the bacterial cell is purified by a combination of polyethylene glycol fractionation, ion exchange chromatography, hydrophobic chromatography, and gel filtration chromatography, to obtain an enzyme, which is characterized by electrophoresis to be a homogenous enzyme.

The activity of the L-ribose isomerase of the invention can be assayed as follows. 0.05 ml of 0.05 M glycine-NaOH buffer (pH 9.0), 0.05 ml of 0.05 M L-ribose and the enzyme solution were mixed together to a total volume of 0.5 ml, for the enzyme reaction at 45° C., to generate L-ribulose, which is assayed by the cysteine/carbazole method. One unit of the enzyme activity is designated as the enzyme amount to generate 1 μmol of L-ribulose per one minute.

The L-ribose isomerase of the invention can be utilized for the conversion reaction between various types of ketose with various types of keto group (C=O) and aldose as substrates, where an alcohol group (HO—C—H) bound to the carbon at position 2 has L-glycero coordination, which are for example L-ribose, L-ribulose, L-allose, L-psicose, D-tagatose, D-tallose, D-mannose, D-fructose, D-lyxose and D-xylulose. Hence, one type of the enzyme can produce various types of sugars, very advantageously industrially.

The thermostable L-ribose isomerase of the invention is not necessarily purified at high purity for use. For example, the microorganism with the thermostable L-ribose isomerase may be treated with toluene for use, advantageously for industrial sugar conversion. Additionally, the thermostable L-ribose isomerase of the invention may be immobilized and used advantageously, by disrupting the bacterial cell by known methods to extract the endogenous thermostable L-ribose isomerase and then immobilizing the enzyme. The microorganism with the enzyme activity or a partially purified enzyme may be immobilized by immobilization methods such as inclusion methods, adsorption methods or covalent bond methods, for repeated use for batch reaction or may be packed in a column for continuous use, appropriately.

As to the reaction temperature, the reaction is performed at a temperature with no inactivation of the enzyme, for example 4 to 60° C., preferably 10 to 50° C. The reaction time may appropriately be selected, depending on the progress level of the enzyme reaction. Generally, the reaction time is about 0.1 to 100 hours when the enzyme is used at an amount of about 0.1 to 100 units per one gram of a solid substrate.

The reaction solution thus obtained contains both aldose and ketose. By general methods, insoluble matters are removed from the reaction solution by filtration, centrifugation and the like. Subsequently, the resulting solution is decolored with activated carbon, desalted with ion exchange resins of H type and $CO_3$ types, and concentrated into a syrup-like product or then dried into a powdery product. Otherwise, the crystal sugar may be prepared finally as a crystal product, optionally. If necessary, further purification at a high level may also be done. By fractionation by ion exchange column chromatography, fractionation with active charcoal column chromatography, fractionation with silica gel column chromatography, and decomposition and removal of ketose with alkali treatment, for example, sugars at higher purity can also be obtained readily. Various sugars thus obtained can advantageously be utilized in various applications such as reagents, sweeteners and quality modifiers in food industries, raw materials and intermediates in pharmaceutical industries and chemical industries.

In particular, D-ribose as an optical isomer of L-ribose is an essential component of RNA with a close relation with cell proliferation. Therefore, L-ribose itself or a derivative thereof as prepared from the raw material L-ribose can be used as an inhibitor of nucleic acid replication, including for example pharmaceutical agents such as antibacterial agents, antiviral agents, anti-HIV agents, and anti-cancer agents. As described above, L-ribose can readily be produced from L-ribulose, using the L-ribose isomerase of the invention. L-Ribulose from any source or any origin may be satisfactory. From a raw material ribitol, for example, L-ribulose can readily be obtained via oxidation reaction with a microorganism of the genus *Gluconobacter* or the genus *Acetobacter*, specifically for example *Gluconobacter flauteurii* or *Acetobacter aceti*.

The invention will now be described below in detail in Examples. The invention is not limited by these Examples.

Example 1

Properties of Purified Enzyme

<Method>

Using 50 mM L-ribose as a substrate, the enzyme reaction continued at 45° C. for 10 minutes, so that the amount of the generated ketose (L-ribulose) was assayed by the cysteine/ carbazole method. As to the temperature stability, the enzyme activity was assayed after 10-min treatment at individual temperatures. As to the optimal pH conditions, the enzyme reaction was performed at 45° C. for 10 minutes in 50 mM acetate buffer (pH 2 to 6), 50 mM sodium phosphate buffer (pH 6 to 8), 50 mM Tris-HCl buffer (pH 8 to 9) or 50 mM glycine-sodium hydroxide buffer (pH 9 to 11), using 50 mM L-ribose as substrate, to assay the amount of a ketose (L-ribulose) generated thereafter by the cysteine/carbazole method (Table 2). The enzyme reaction was done at the composition shown in Table 2 at 45° C. for 10 minutes (Table 3), and the reaction was terminated by adding 50 μl of 10% TCA (trichloroacetic acid). As shown in Table 2, the cysteine/carbazole method comprised sequentially adding 100 μl of 1.5% cysteine solution and 3 ml of 70% sulfuric acid to 0.5 ml of a sample after the enzyme reaction, for agitation; the resulting mixture was left in water, to which 100 μl of 0.12% carbazole solution was added for reaction at 20° C. for 20 minutes. After completion of the reaction, absorbance at 540 nm was measured with an ultraviolet/visible spectrophotometer V530 (JASCO Corporation). Additionally, the amount of the enzyme generating 1 μmol L-ribulose per one minute was designated as one unit.

TABLE 2

Cysteine/carbazole method 0.5 ml sample
⬅ 0.1 ml 1.5% Cysteine
⬅ 3.0 ml 70% H$_2$SO$_4$
⬅ 0.1 ml 0.12% carbazole 50° C., 30 min: Hexose 35° C., 20 min: Pentose 20° C., 20 min: Riburose Absorbance at 580 nm (Hexose) or at 540 nm (Pentose)

TABLE 3

| | |
|---|---|
| Substrate (50 mM) | 50 μl |
| Buffer (50 mM) | 350 μl |
| MnCl$_2$ 10 mM | 50 μl |
| Enzyme | 50 μl |

(Enzyme Purification)

The bacterial strain MB426 of the invention was cultured in 3 L of a culture broth supplemented with 0.1% D-lyxose in 2% TSB at 37° C. for 2 days, to extract a crude enzyme solution by ultrasonication. The crude enzyme solution was fractionated with ammonium sulfate; subsequently, L-ribose isomerase was purified by chromatography on individual columns packed with Q-Sepharose, Resource-Q and phenyl Sepharose, in this order. It was confirmed by SDS-PAGE (SDS-polyacrylamide gel electrophoresis) that the resulting L-ribose isomerase was a single enzyme with no contamination. The purified enzyme was at 0.814 U/mg, as obtained at a yield of 7.4%.

Figure 1:
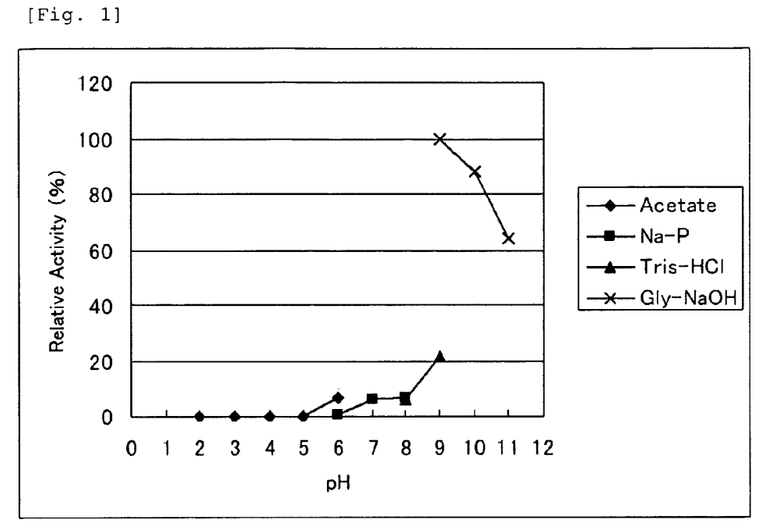
FIG. 1 is a view showing the effect of pH on the activity of the thermostable L-ribose isomerase derived from *Raoultella ornithinolytica*. In the table, "Acetate" denotes 50 mM acetate buffer (pH 2 to 6); Na—P denotes 50 mM sodium phosphate buffer (pH 6 to 8); Tris-HCl denotes 50 mM Tris-HCl buffer (pH 8 to 9); and Gly-NaOH denotes 50 mM glycine-sodium hydroxide buffer (pH 9 to 11). The condition using Gly- NaOH, pH 9.0 is the optimal condition (optimal pH) for the enzyme. The enzyme exerts extremely low activity in the Tris-HCl buffer at the same pH, which is generally due to the non-antagonistic inhibition of the isomerase activity with Tris.
Figure 2:
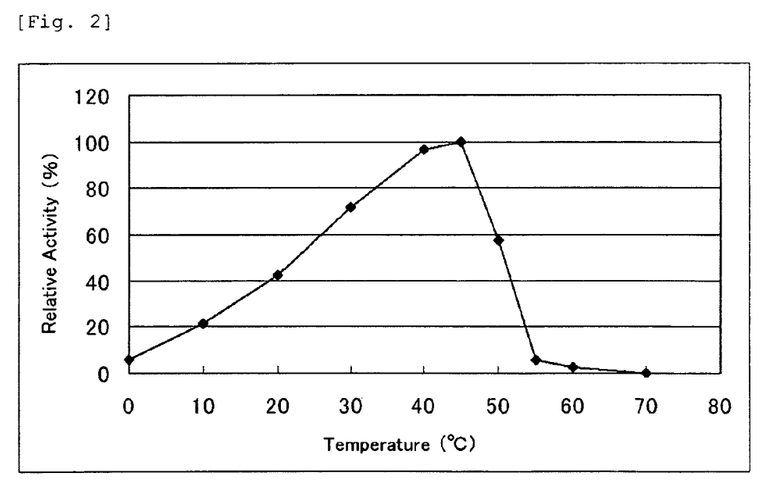
FIG. 2 is a view showing the effect of temperature on the activity of the thermostable L-ribose isomerase derived from *Raoultella ornithinolytica*. The condition using 45° C. is the optimal condition (optimal temperature) for the enzyme.
Figure 3:
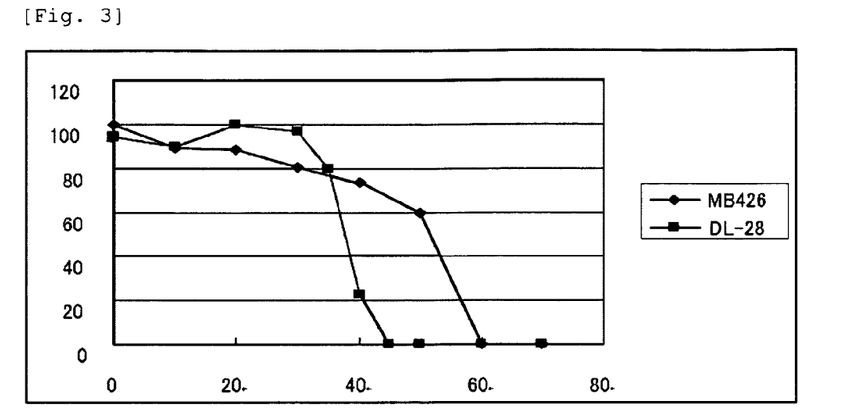
FIG. 3 is a view showing the temperature stability of the thermostable L-ribose isomerase derived from *Raoultella ornithinolytica* (described as MB426) in comparison with the temperature stability of the L-ribose isomerase derived from *Acinetobacter calcoaceticus* (described as DL-28). The graph shows that the temperature stability of the L-ribose isomerase of the invention is greater than the temperature stability of the L-ribose isomerase derived from *Acinetobacter calcoaceticus*.

<Properties of Purified Enzyme>
Molecular weight: 32,000 (SDS-PAGE)
Optimal pH: pH 9.0 (glycine-NaOH buffer) (FIG. 1)
Optimal temperature: 45° C. (FIG. 2)
Temperature stability: stable up to 45° C. during thermal treatment at pH 9.0 for 10 minutes.
DL-28 represents the results with *Acinetobacter* sp. strain DL-28 (accession No. FERM BP-5335 described in the patent reference 1), showing the temperature stability of the DL-28 strain-derived L-ribose isomerase with not so good thermal stability, for comparison. Compared with the enzyme generated by the *Acinetobacter* sp. strain DL-28, the present enzyme had temperature stability by about 15° C. higher than that of the enzyme under the same conditions, indicating that the present enzyme had higher thermal stability.

[Substrate Specificity]

According to the assay method of the activity, the activity of the enzyme was assayed, using various aldose types as substrates. The activities on various aldose types are shown in relative activities to the activity on L-ribose, which is designated as 100%.

TABLE 4

| | |
|---|---|
| L-Ribose: | 100 |
| D-Tallose: | 56.9 |
| D-Lyxose: | 15.3 |
| L-Allose: | 2.2 |

Figure 4:
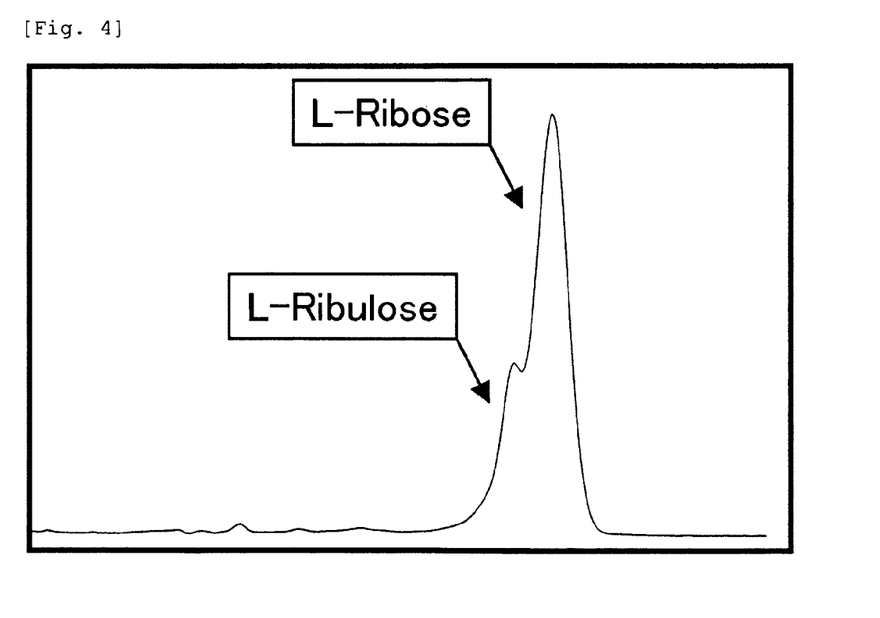
FIG. 4 is a view showing the reaction of the substrate L-ribose with the thermostable L-ribose isomerase derived from *Raoultella ornithinolytica* to generate L-ribulose.
Figure 5:
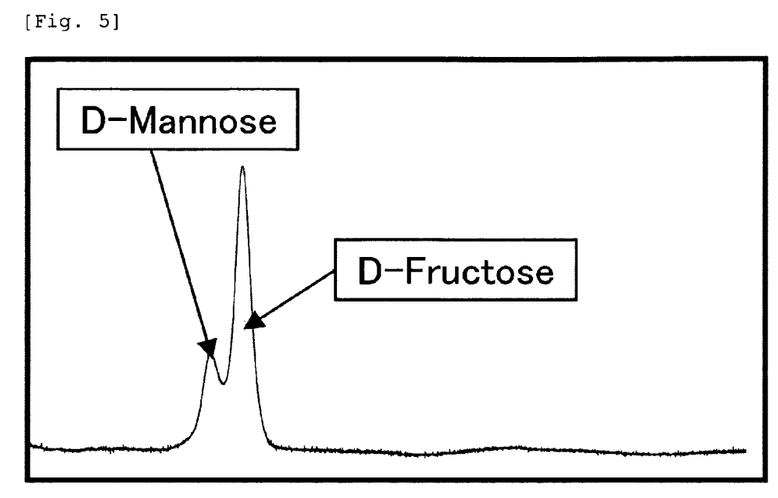
FIG. 5 is a view showing the reaction of the substrate D-fructose with the thermostable L-ribose isomerase derived from *Raoultella ornithinolytica* to generate D-mannose.
Figure 6:
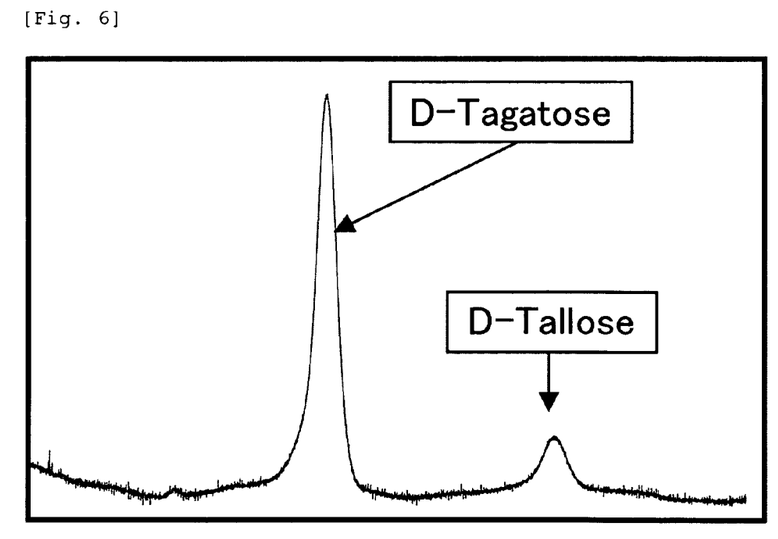
FIG. 6 is a view showing the reaction of the substrate D-tagatose with the thermostable L-ribose isomerase derived from *Raoultella ornithinolytica* to generate D-tallose.
Figure 7:
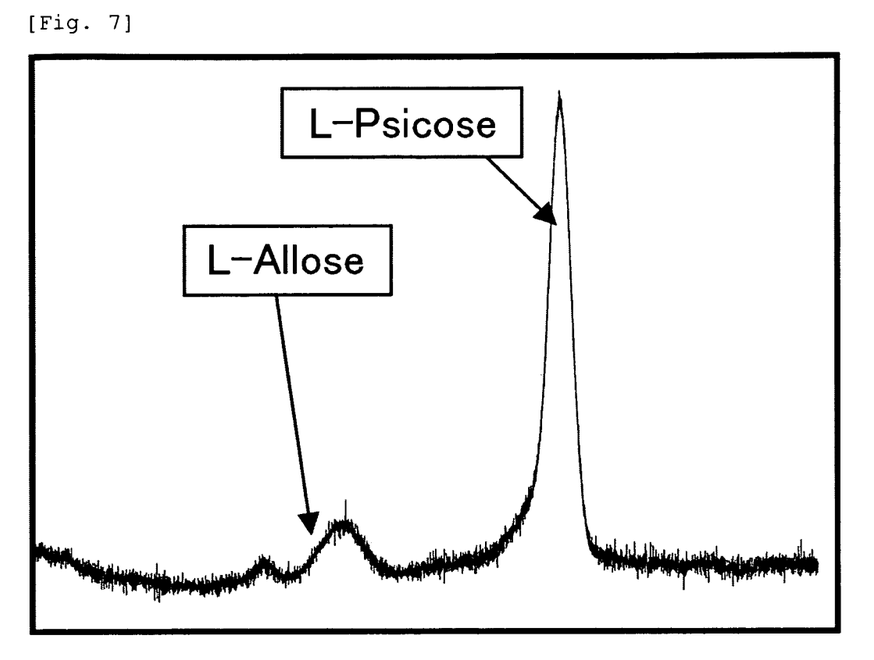
FIG. 7 is a view showing the reaction of the substrate L-psicose with the thermostable L-ribose isomerase derived from *Raoultella ornithinolytica* to generate L-allose.

FIG. 4 shows that L-ribulose is generated via reaction of the substrate L-ribose with the thermostable L-ribose isomerase from *Raoultella ornithinolytica*; FIG. 5 shows that D-mannose is generated via reaction of the substrate D-fructose therewith; FIG. 6 shows that D-tallose is generated via reaction of the substrate D-tagatose therewith; and FIG. 7 shows that L-allose is generated via reaction of the substrate L-psicose therewith.

(Confirmation of Enzyme Reaction Product)

A crude enzyme solution (0.65 U/ml) was recovered after culturing in a culture medium with 0.1% D-lyxose in 2% TSB, at 37° C. for 2 days and ultrasonication for extraction; 150 μl of the crude enzyme solution reacted with 50 mM of a substrate including individual ketose types such as L-ribose, D-fructose, D-tagatose and L-psicose at 40° C. for 24 hours. After reaction, the enzyme was inactivated under heating in hot water for 2 minutes, and centrifuged at 12,000 rpm for 5 minutes to recover the supernatant. Then, about 2 spoonfuls of a desalted resin (mixed and dried at a ratio of IRA411: SKIB=2:1) in a microspatula were added to the resulting supernatant, for mixing under inversion. After one hour, the solution was filtered through a 0.45-μm filter, for high-performance liquid chromatography (HPLC). As the column, Hitachi HPLC column GL-C611 (manufactured by Hitachi Chemical Industry Co., Ltd.) was used; as the detector, a differential refractive meter (L-7490 refractive index detector manufactured by Hitachi Hightech Co., Ltd.) was used. While the column was retained at 60° C., $10^{-4}$ M sodium hydroxide solution as an eluent was used at a flow rate of 1.0 mL/min. The resulting signals were collected and analyzed with a data analysis software (SmartChrom, manufactured by KYA Technologies Co., Ltd.).

As shown in the results in Table 2, the enzyme exerted the highest activity for L-ribose. Other than the activity, the enzyme exerted activities for D-tallose, D-lyxose, D-mannose and L-allose. The reaction modes with these aldose and ketose types were examined. Consequently, their reaction modes are common. As one example, the reaction mode with L-ribose is shown below in Chemical Formula 1.

[Chemical formula 1]

L-Ribose → L-Ribulose

As apparently shown in Chemical formula 1, the L-ribose isomerase of the invention reacts with aldose and aldoketose, where the alcohol group bound to the carbon at position 2 (OH—C—H) has L-glcyero coordination. However, the L-ribose isomerase of the invention never exerts any activities for D-glucose, D-allose and D-altrose, where the alcohol group bound to the carbon at position 2 (OH—C—H) has D-glcyero coordination.

INDUSTRIAL APPLICABILITY

As apparent from above description, the L-ribose isomerase of the invention can advantageously be utilized for conversion of various types of sugars, with no need of purification at a higher level, so the L-ribose isomerase can advantageously be utilized for industrial production of rare sugars. In accordance with the invention, diverse types of rare sugars extremely hardly available conventionally can readily be provided, so that such rare sugars may influence various fields such as foods, cosmetics, pharmaceutical products and chemical industries, very meaningfully industrially.

The invention claimed is:

1. An isolated thermostable L-ribose isomerase with the following physico-chemical properties and with an action to isomerize L-ribose to generate L-ribulose or to isomerize L-ribulose to generate L-ribose inversely:
   1) molecular weight: 32,000 (SDS-PAGE);
   2) optimal temperature: 45° C.;
   3) optimal pH: pH 9.0 (glycine-NaOH buffer);
   4) temperature stability; stable up to 45° C., during thermal treatment at pH 9.0 for 10 minutes,
   wherein said isolated thermostable L-ribose isomerase is an enzyme isolated from *Raoultella ornithinolytica* strain MB426 (NITE BP-277).

2. A method for producing a thermostable L-ribose isomerase comprising culturing a microorganism with an ability to generate L-ribose isomerase, and collecting a thermostable L-ribose isomerase with the following physico-chemical properties and with an action to isomerize L-ribose to generate L-ribulose or to isomerize L-ribulose to generate L-ribose inversely, from the culture:
   1) molecular weight: 32,000 (SDS-PAGE);
   2) optimal temperature: 45° C.;
   3) optimal pH: pH 9.0 (glycine-NaOH buffer);
   4) temperature stability; stable up to 45° C., during thermal treatment at pH 9.0 for 10 minutes,
   wherein said microorganism is *Raoultella ornithinolytica* strain MB426 (NITE BP-277).

3. An isolated microorganism belonging to the genus *Raoultella* with an ability to generate a thermostable L-ribose isomerase with the following physico-chemical properties and with an action to isomerize L-ribose to generate L-ribulose or to isomerize L-ribulose to generate L-ribose inversely:
   1) molecular weight: 32,000 (SDS-PAGE);
   2) optimal temperature: 45° C.;
   3) optimal pH: pH 9.0 (glycine-NaOH buffer);
   4) temperature stability; stable up to 45° C., during thermal treatment at pH 9.0 for 10 minutes,
   wherein said isolated microorganism is *Raoultella ornithinolytica* strain MB426 (NITE BP-277).

4. A method for producing a ketose, comprising allowing a thermostable L-ribose isomerase according to claim 1 to interact with an aldose selected from L-ribose, D-lyxose, D-tallose, D-mannose, L-allose, and L-gulose and collecting a ketose selected from the individually corresponding generated L-ribulose, D-xylulose, D-tagatose, D-fructose, L-psicose and L-sorbose.

5. A method for producing a ketose according to claim 4, wherein said thermostable L-ribose isomerase is obtained by toluene treatment of said microorganism or is an immobilized thermostable L-ribose isomerase obtained from said microorganism.

6. A method for producing an aldose, comprising allowing a thermostable L-ribose isomerase according to claim 1 to interact with a ketose selected from L-ribulose, D-xylulose, D-tagatose, D-fructose, L-psicose and L-sorbose and collecting an aldose selected from the individually corresponding generated L-ribose, D-lyxose, D-tallose, D-mannose, L-allose and L-gulose.

7. A method for producing an aldose according to claim 6, wherein said thermostable L-ribose isomerase is obtained by toluene treatment of said microorganism or is an immobilized thermostable L-ribose isomerase obtained from said microorganism.

8. A conversion method between an aldose and a ketose, comprising allowing a thermostable L-ribose isomerase according to claim 1 to interact with an aldose selected from L-ribose, D-lyxose, D-tallose, D-mannose, L-allose, and L-gulose to isomerizes the aldose to corresponding a ketose selected from L-ribulose, D-xylulose, D-tagatose, D-fructose, L-psicose and L-sorbose or comprising allowing a thermostable L-ribose isomerase to interact with a ketose selected from L-ribulose, D-xylulose, D-tagatose, D-fructose, L-psicose and L-sorbose to isomerizes the ketose to corresponding an aldose selected from L-ribose, D-lyxose, D-tallose, D-mannose, L-allose and L-gulose.

9. A conversion method between an aldose and a ketose according to claim 8, wherein said thermostable L-ribose isomerase is obtained by toluene treatment of said microorganism or is an immobilized thermostable L-ribose isomerase obtained from said microorganism.

10. A method for producing L-ribose comprising a step of allowing a thermostable L-ribose isomerase according to claim 1 to interact with L-ribulose and a step of colleting the generated L-ribose.

11. A method for producing L-ribose according to claim 10, where the L-ribulose is obtained by oxidizing ribitol with a microorganism belonging to the genus *Glucobacter* or the genus *Acetobacter*.

12. A method for producing L-ribose according to claim 10, wherein said thermostable L-ribose isomerase is obtained by toluene treatment of said microorganism or is an immobilized thermostable L-ribose isomerase obtained from said microorganism.

13. A method for producing L-ribose according to claim 10, where the generated L-ribose is collected through a step including filtration, centrifugation, decoloring, desalting, concentration, drying, column chromatography, crystallization or sugar fractionation.

14. A method for producing L-ribose according to claim 13, where an ion exchange resin is used for column chromatography.

* * * * *